United States Patent
Kulkarni et al.

(10) Patent No.: US 6,955,903 B2
(45) Date of Patent: Oct. 18, 2005

(54) PREBLEND OF MICROCRYSTALLINE CELLULOSE AND LACTASE FOR MAKING TABLETS

(75) Inventors: Sunanda R. Kulkarni, N. Wales, PA (US); Robert T. McFadden, Congers, NY (US); David H. Rogers, Ambler, PA (US); James T. Walter, Jr., Ambler, PA (US)

(73) Assignee: McNeil-PPC, Skillman, NJ (US)

(*) Notice: Subject to any disclaimer, the term of this patent is extended or adjusted under 35 U.S.C. 154(b) by 0 days.

(21) Appl. No.: 10/001,733

(22) Filed: Nov. 2, 2001

(65) Prior Publication Data

US 2002/0187536 A1 Dec. 12, 2002

Related U.S. Application Data

(62) Division of application No. 09/526,627, filed on Mar. 16, 2000, now abandoned, which is a division of application No. 08/496,824, filed on Jun. 29, 1995, now Pat. No. 6,057,139.

(51) Int. Cl.$^7$ .......................... C12N 9/96; C12N 11/12; A61K 38/47; A61K 9/20
(52) U.S. Cl. ................. 435/188; 424/94.61; 424/464; 424/465; 435/179; 435/200; 435/207
(58) Field of Search ........................ 435/188, 179, 435/200, 207; 424/94.61, 464, 465

(56) References Cited

U.S. PATENT DOCUMENTS

| | | | |
|---|---|---|---|
| 2,681,858 A | 6/1954 | Stimpson | |
| 2,781,266 A | 2/1957 | Stimpson | |
| 2,809,113 A | 10/1957 | Stimpson | |
| 2,826,503 A | 3/1958 | Roberts et al. | |
| 3,592,739 A | 7/1971 | Stemberg | |
| 3,629,073 A | 12/1971 | Cayle | |
| 3,718,739 A | 2/1973 | Cayle | |
| 3,816,259 A | 6/1974 | Collinge et al. | |
| 3,919,049 A | 11/1975 | Kiuchi et al. | |
| 3,954,979 A | 5/1976 | Bowman | |
| 4,034,035 A | 7/1977 | Schwartz et al. | |
| 4,079,125 A | 3/1978 | Sipos | |
| 4,229,539 A | 10/1980 | Miwa et al. | |
| 4,435,389 A | 3/1984 | Mutai et al. | |
| 4,447,412 A | 5/1984 | Bilton | |
| 4,895,801 A | 1/1990 | Kan et al. | |
| 4,957,860 A | 9/1990 | Kan et al. | |
| 5,387,422 A | 2/1995 | Handel et al. | |
| 5,637,561 A * | 6/1997 | Shen et al. | 514/2 |
| 6,057,139 A | 5/2000 | Kulkarni et al. | |
| 6,139,865 A | 10/2000 | Friend et al. | |
| 6,149,941 A | 11/2000 | Schwarz et al. | |
| 6,153,220 A | 11/2000 | Cumming et al. | |
| 6,165,512 A | 12/2000 | Mezaache et al. | |
| 6,228,397 B1 | 5/2001 | Shen et al. | |
| 6,365,208 B1 * | 4/2002 | Kulkarni et al. | 426/61 |
| 6,410,018 B1 * | 6/2002 | Eisenhardt et al. | 424/94.6 |
| 6,428,786 B1 * | 8/2002 | Eisenhardt et al. | 424/94.6 |

FOREIGN PATENT DOCUMENTS

| | | |
|---|---|---|
| DE | 2554407 | 6/1976 |
| JP | 5115686 | 7/1974 |

* cited by examiner

*Primary Examiner*—David M. Naff

(57) ABSTRACT

A preblend for making lactase tablets is prepared containing about 1–99% (preferably about 200–60%) by weight lactase and about 1–99% (preferably about 40–80%) by weight microcrystalline cellulose. Lactase used in the preblend may be in combination with up to about 4 parts (preferably about 0.5–2 parts) by weight cutting agent such as sugars, starches, cellulose, and inorganic salts for each part by weight lactase. About 0.5–4% by weight lubricant such as magnesium stearate may be present in the preblend. A preferred preblend contains about 9.6 weight percent lactase and about 90 weight percent microcrystalline cellulose, or about 2000 to about 9000 FCC lactase units and from about 40 to about 80 weight percent microcrystalline cellulose. Another preferred preblend contains about 9.6 weight percent lactase, about 30.0 weight percent microcrystalline cellulose and about 59.4 weight percent mannitol. Each preblend may also contain magnesium stearate. A preferred lactase is from *Aspergillus oryzae* and the microcrystalline cellulose preferably has an average particle size of about 10–200 µm.

10 Claims, No Drawings

US 6,955,903 B2

PREBLEND OF MICROCRYSTALLINE CELLULOSE AND LACTASE FOR MAKING TABLETS

This application is a division of U.S. patent application Ser. No. 09/526,627, filed Mar. 16, 2000, now abandoned, which was a division of U.S. patent application Ser. No. 08/496,824, filed Jun. 29, 1995, now U.S. Pat. No. 6,057, 139.

The present invention relates to lactase tablets having improved content uniformity, especially of the active ingredient. More particularly, the present invention relates to a preblend of microcrystalline cellulose and lactase for the manufacture of tablets having improved content uniformity.

BACKGROUND OF THE INVENTION

Lactose, or milk sugar, is a disaccharide carbohydrate which is hydrolyzed during the digestive process to glucose and galactose. This hydrolysis is catalyzed by the enzyme lactase, or beta-galactosidase. Although this enzyme is normally present in the intestinal juices and mucosa, investigations have shown that a significant portion of the population is lactose intolerant or lactase deficient. Consequently, there has been a great demand for a dietary supplement of lactose-hydrolyzing lactase enzymes in lactose intolerant individuals.

Commercially available tablets containing lactase have been observed to have an undesireably short shelf-life. Generally, it is desirable to have a shelf-life beyond about 24 months.

Shelf-life, as used herein for a lactase tablet product, is the time it takes for the lower 95% confidence interval of the product's potentcy plotted versus time to fall below a predetermined lower specification limit. Thus, it can be seen that shelf-life is a function of lactase content uniformity in the tablets and the inherent lactase chemical stability. It is an object of the present invention to formulate a lactase containing tablet composition having improved chemical stability.

SUMMARY OF THE INVENTION

Breifly, there is provided by the present invention a preblend for the manufacture of lactase tablets consisting essentially of:

a) from about 1% to about 99% by weight of a combination of lactase and cutting agent where said combination has from 0 to about 4 parts by weight cutting agent for each part by weight lactase; and b) from about 1% to about 99% by weight of microcrystalline cellulose.

DETAILED DESCRIPTION OF THE INVENTION

Lactose hydrolyzing lactase enzymes are known to be produced by various yeasts, bacteria and fungi. Among the organisms heretofore disclosed as useful for this purpose are yeasts, such as, *Saccharomyces fragilis, Torula cremoris* and *Torula utilis*, bacteria, such as, *Escherichia coli* and *Lactobacillus bulgaricus*, fungi, such as, *Aspergillus oryzae, Aspergillus flavus* and *Aspergillus niger*, and various other micro-organisms, such as, those described in U.S. Pat. Nos. 2,681,858, 2,781,266 and 2,809,113. The lactase enzyme preparations produced by these organisms generally have pH optimums on the alkaline side or in the weakly acid pH range of about 5–7. Yeasts, which are the primary source of commercial lactases, are known to produce lactases having pH optimums of about 7. Most of these conventional lactase enzyme preparations contain other proteins in admixture therewith. When lactase is referred to herein, it is such an admixture that is referred to.

As seen, lactase enzymes are commercially produced as biological products which have a variability in potentcy from batch to batch that requires adjustment with a cutting agent in order to produce a uniform commercial product. Cutting agent is added to the lactase enzyme product and the amount is adjusted from batch to batch to produce a lactase enzyme product of the target potentcy. Cutting agents may be selected from any inert pharmaceutical excipient, including, sugars, starches, cellulose and inorganic salts. The amount or even the absence of the cutting agent herein is not critical to the present invention. Of course, it is desireable in the practice of the present invention that the lactase be in a readily available and convenient form of known potentcy for addition to the formulation. Suitable cutting agents include dextrose, mannitol, calcium phosphate, sodium citrate and microcrystalline cellulose.

Suitable lactase for use herein include, a lactase isolated from *Saccharomyces lactis*, by Gist-Brocade in Delft, Holland, and sold by Enzyme Development Corporation, New York, N.Y.; a lactase from *Aspergillus oryzae*. Lactase Y-400, produced by K. K. Yakult Honsha; a lactase from *Aspergillus oryzae*. Plexazym LA 1, produced by Roehm GmbH; a lactase from *Aspergillus oryzae*, produced by Shinnihon Kagaku Kogyo Co.; a lactase from *Kluyveromyces fragilis* produced by Sturges Enzymes, Selby, North Yorkshire, England; a lactase from *Aspergillus oryzae*, Takamine lactase, produced by Miles Laboratories, Inc., Elkhart, Ind.; and a lactase from *Kluyveromyces fragilis* produced by Novo Enzymes, Bagsvaerd, Denmark. These suppliers and others offer, generally, lactase, including a cutting agent, having a potency of between 14,000 and 100,000 FCC lactase units/gram. Preferably, the combination of lactase and cutting agent is present in a lactase tablet formulation in an amount of from about 5% to about 15% by weight and said combination has from about 0 to about 3 parts by weight cutting agent and more preferably from about 0.5 to about 2 parts by weight for each part by weight lactase. A preferred lactase for use herein is from *Aspergillus oryzae* produced by Amano Pharmaceutical Company, LTD. under the trade name Lactase F "Amano" 100. This preferred lactase contains, on a weight basis, about 50% a mixture containing sodium citrate and dextrose and the balance of lactase and has a potency of 100,000 FCC lactase units/gram.

Microcrystalline cellulose is manufactured by the controlled hydrolysis of alpha-cellulose, obtained as a pulp from fibrous plant materials, with dilute mineral acid solutions. Following hydrolysis, the hydrocellulose is purified by filtration and the aqueous slurry is spray dried to form dry, porous particles of a broad size distribution. Suitable microcrystalline cellulose will have an average particle size of from about 20 to about 200 $\mu$m. Microcrystalline cellulose is available from several suppliers. Suitable microcrystalline cellulose includes Avicel PH 101, Avicel PH 102, Avicel PH 103, Avicel PH 105 and Avicel PH 200, manufactured by FMC Corporation. Preferrably the microcrystalline cellulose is present in a lactase tablet formulation in an amount of from about 25% to about 70% by weight.

According to the present invention, improved content uniformity in the lactase tablet may be obtained by first mixing the lactase, optionally including the cutting agent, with the microcrystalline cellulose to make a preblend. Preferably, the preblend contains from about 15% to about 75% by weight the combination of lactase and cutting agent and from about 25% to about 85% microcrystalline cellulose. More preferably, the preblend contains from about 20% to about 60% by weight the combination of lactase and cutting agent and from about 40% to about 80% microcrystalline cellulose. Subsequently, other desired ingredients may be added to obtained a mixture suitable for compressing into a tablet. Although following the mixing of the preblend, the order of addition of the other desired ingredients is not critical, it is the practice in formulating tablets, that the lubricant is added as a last ingredient before compression.

The list of possible other desired ingredients is extensive, but in the case of compressing tablets should at least include a lubricant. This list might include conventional solid fillers or carriers, such as, cornstarch, calcium phosphate, calcium sulfate, calcium stearate, stearic acid, glyceryl mono- and distearate, sorbitol, mannitol, gelatin, natural or synthetic gums, such as, carboxymethyl cellulose, methyl cellulose, alginate, dextran, acacia gum, karaya gum, locust bean gum, tragacanth and the like, diluents, binders, lubricants, disintegrators, coloring and flavoring agents.

A preferred other ingredient to make a preferred chewable tablet herein is mannitol. The mannitol should be ground to have an average particle size of between about 50 $\mu$m and about 500 $\mu$m prior to formulating. Preferrably the mannitol is present in a lactase tablet formulation in an amount of from about 25% to about 70% by weight.

Examples of the lubricants include magnesium stearate, talc, polyethylene glycol, silica and hardened vegetable oils. The preferred lubricant is magnesium stearate. Preferably, the lubricant is present in a lactase tablet formulation in an amount of from about 0.25% to about 6% and most preferably from about 0.5% to about 4% by weight.

The quantity of lactase enzyme administered in a single oral dosage can vary within wide limits. This quantity will depend on factors which include the lactase activity of the lactase enzyme, the magnitude of the lactase deficiency or lactose intolerance in the particular individual requiring the dietary supplement of lactase and the dietary habits of the individual. As a general matter, the affected individual will become accustomed to estimating a required dose based on the particular facts and experience.

Ideally, the lactase tablets herein should contain sufficient lactase to satisfy the dosage requirement of most individuals requiring the dietary supplement of lactase in most situations. Alternatively, the lactase tablets herein should contain a fraction of such a dose so that the gamut of affected individuals can closely match their dosage requirements with the administration of one, two or three tablets. In the first case, a tablet herein might contain 9000 FCC lactase unit I tablet and, in the second case, 3000 FCC lactase unit/tablet.

The following examples are intended to illustrate the invention herein and are in no way intended to be limiting:

EXAMPLE 1

The dry blends of Table 1 were prepared as follows containing the ingredients as shown. For each blend, the ingredients were delumped by screening through a hand screen, blended for 20 minutes in a twin shell blender. The lactase employed was Lactase F "Amano" 100, as described above, and the microcrystalline cellulose was Avicel PH 102, with an average particle size of 100 $\mu$m. The units of the ingredients in Table 1 are in parts by weight.

For each blend, 25 g samples were placed in plastic bottles and lapel sealed. Bottles of each blend were stored at 4 stablility stations providing for 4 different conditions: at 4° C.; at room temperature; at room temperature and 90% R. H.; and at 30° C. Initially a bottle of each blend was taken and at 2 weeks, and one month a bottle of each blend was taken from each station. Three samples (where a sample is the equivalent of 10 tablets) from each bottled were assayed for active lactase content or lactase activity. An assay mean and RSD (relative standard deviation) was determined for each station/time point, based on these three assay values. The average assay variability for each blend was compared by averaging the assay RSDs across the stability stations tested for the initial, 2 weeks, and 1 month time points. As seen in Table 1, the variability of the microcrystalline preblend was unexpectedly low as compared to the other excipients and, in fact, was on par with the variability of the bulk enzyme.

Lactase activity was determined by an adaptation of the method described in the *Food Chemicals Codex*, National Academy Press, 1981, pages 491–492, using o-nitrophenyl-$\beta$-D-galactopyranoside as substrate incubated at pH 4.5 and 37° C. Analyses were performed as described with the following modifications. The standard preparation was changed from the published 1% sodium bicarbonate solution to a solution prepared in 1% sodium carbonate in order to match the composition of the final stopped reaction mixture. A single standard of 0.14 mM o-nitrophenyl was used. The assay volumes were reduced by half (2.0 mL of substrate solution and 0.5 mL of test solution) in order to perform the final dilution in the orginal test tube.

TABLE 1

| Blend | 1 | 2 | 3 | 4 | 5 | 6 |
|---|---|---|---|---|---|---|
| lactase | 100 | 10 | 10 | 10 | 10 | 10 |
| microcrystalline cellulose | — | 90 | — | — | — | — |
| mannitol | — | — | 89 | — | — | — |
| Mg stearate | — | — | 1 | — | — | — |
| dicalcium phosphate | — | — | — | 90 | — | — |
| dextrates | — | — | — | — | 90 | — |
| sucrose (compressible) | — | — | — | — | — | 90 |
| Average Assay RSD | 2.4 | 2.3 | 7.9 | 7.0 | 14.5 | 14.6 |

EXAMPLE 2

A blend was prepared containing the following ingredients in percent by weight:

| | |
|---|---|
| lactase | 9.6 |
| microcrystalline cellulose | 30.0 |
| granular mannitol | 59.4 |
| magnesium stearate | 1.0 |

The lactase employed was Lactase F "Amano" 100, as described above, and the microcrystalline cellulose was Avicel PH 102, with an average particle size of 100 $\mu$m. The microcrystalline cellulose and lactase were combined in a gravity blender and blended for 15 minutes, 30 ft$^3$, 14–16 rpm. The mannitol was delumped by passing it through a #10 screen, combined with the microcrystalline cellulose/lactase blend and the resulting combination was blended an additional 10 minutes. The magnesium stearate was delumped by passing it through a #20 mesh screen, combined with the mannitol/microcrystalline cellulose/lactase blend and the resulting combination was blended an additional 10 minutes. This final combination was compressed into tablets.

What is claimed is:

1. A preblend for the manufacture of lactase tablets comprising:

from about 3000 to about 9000 FCC lactase units;

and from about 40 to about 80 weight percent microcrystalline cellulose.

2. The preblend of claim 1 which additionally contains a lubricant.

3. The preblend of claim 2 in which the lubricant is magnesium stearate.

4. The preblend of claim 3 in which the magnesium stearate is provided at a level of from about 0.25 to about 6 weight percent.

5. The preblend of claim 4 in which the magnesium stearate is provided at a level of from about 0.5 to about 4 weight percent.

6. A tablet formed from the preblend of claim 1.

7. A tablet formed from the preblend of claim 2.

8. A tablet formed from the preblend of claim 3.

9. A tablet formed from the preblend of claim 4.

10. A tablet formed from the preblend of claim 5.

* * * * *